United States Patent [19]

Hess

[11] Patent Number: 5,370,130
[45] Date of Patent: Dec. 6, 1994

[54] ADJUSTABLE CONDOM RESTRAINER RING STRUCTURE BY AN ELONGATED FUNICLE

[76] Inventor: Robert Hess, 804 Moore Dr., Chelsea, Mich. 48118

[21] Appl. No.: 101,225

[22] Filed: Aug. 3, 1993

[51] Int. Cl.$^5$ .................................................. A61F 6/04
[52] U.S. Cl. ........................................ 128/844; 128/842
[58] Field of Search ............... 128/844, 842, 918; 606/203; 602/79; 604/351, 353; 24/17 B, 482; 600/38, 39, 41; 206/69

[56] References Cited

U.S. PATENT DOCUMENTS

| | | | |
|---|---|---|---|
| D. 311,252 | 10/1990 | Pettway . | |
| D. 314,827 | 2/1991 | Hendren . | |
| 268,407 | 12/1882 | Hughes | 606/203 |
| 2,705,951 | 4/1955 | Crowner | 128/844 |
| 3,845,760 | 11/1974 | Birman | 606/203 |
| 3,910,280 | 10/1975 | Talonn | 606/203 |
| 4,354,494 | 10/1982 | Hogin . | |
| 4,955,392 | 9/1990 | Sorkin . | |
| 4,966,594 | 10/1990 | Thomas | 604/353 |
| 5,111,831 | 5/1992 | Foggia . | |

FOREIGN PATENT DOCUMENTS

| | | | |
|---|---|---|---|
| 2622434 | 5/1989 | France | 604/353 |
| 1252255 | 11/1971 | United Kingdom . | |
| 1259284 | 1/1972 | United Kingdom . | |
| 2137097 | 10/1984 | United Kingdom | 128/844 |

*Primary Examiner*—Robert A. Hafer
*Assistant Examiner*—Michael O'Neill
*Attorney, Agent, or Firm*—Dykema Gossett

[57] ABSTRACT

A combination of a condom and a condom retainer ring structure has an elongated thin-walled tubular sheath of resilient material that is closed at one end and open at the other end. A first ring at the periphery of the opening surrounds the sheath. A second ring adjacent is attached to and adjacent the first ring, with a bridge joining the rings. In use, the first ring and sheath are worn on the shaft of the penis and the second ring encircles the scrotum to anchor the condom. The condom may be made by a method involving a dipping process and by which the two rings are formed individually or by cutting a thick bead rolled from latex coating on a mandrel.

3 Claims, 3 Drawing Sheets

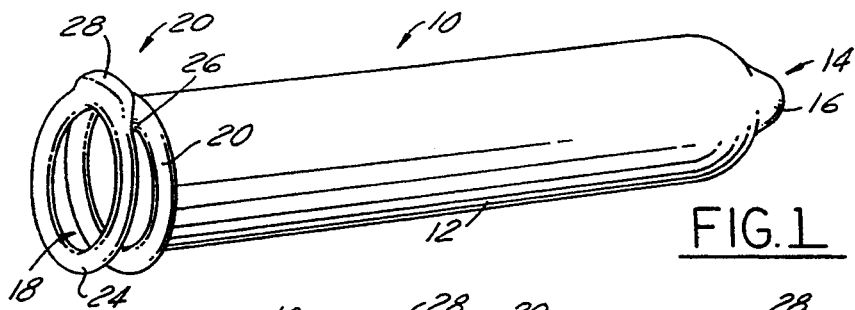
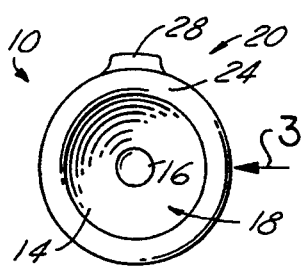
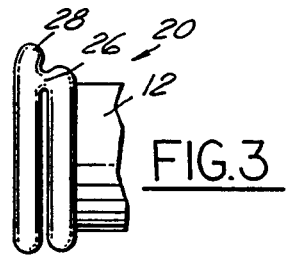
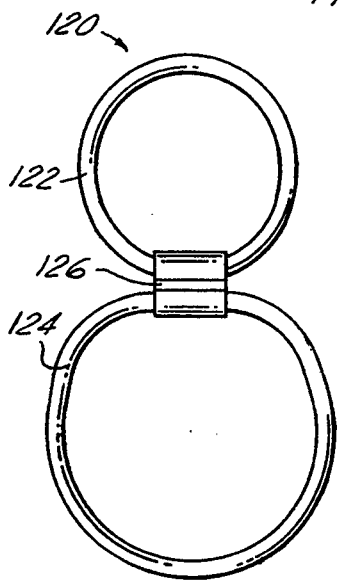
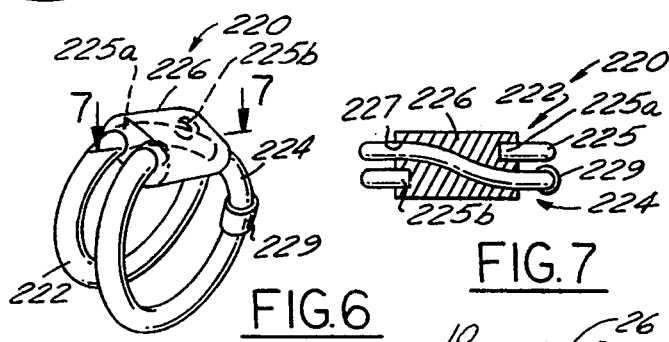
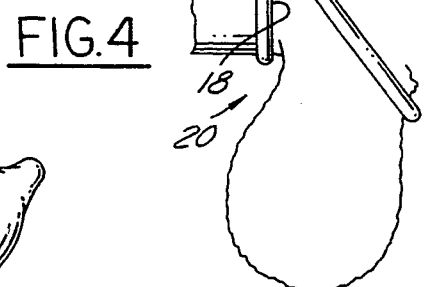
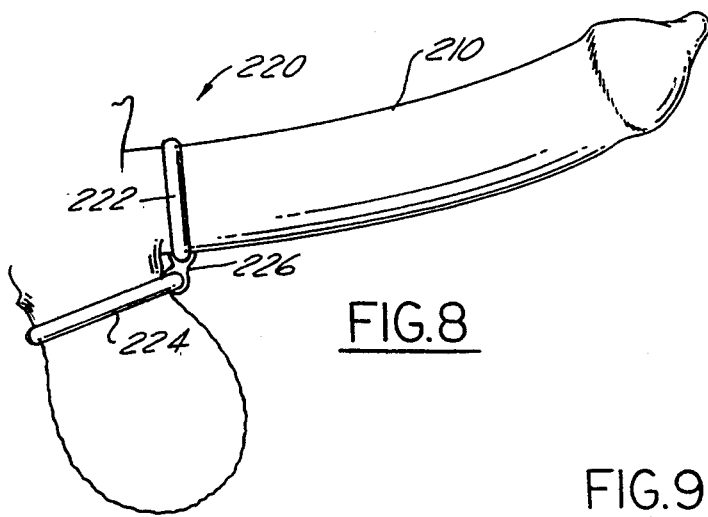
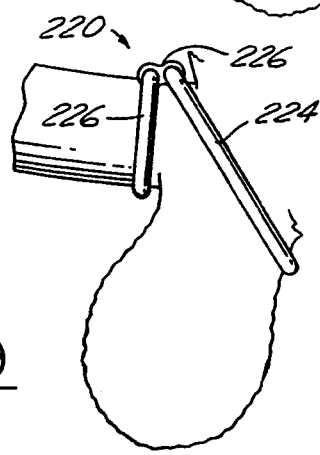

ADJUSTABLE CONDOM RESTRAINER RING STRUCTURE BY AN ELONGATED FUNICLE

BACKGROUND OF THE INVENTION

I. Field of the Invention

The present invention pertains to condoms, and more particularly, to a condom retainer ring structure for retaining a condom on the penis of the wearer by using the scrotum of the wearer as anchorage.

II. Description of the Prior Art

Condoms have conventionally been used for birth control, whereby the sperm carrying semen of a male is prevented from entering the uterus of a female as semen is trapped in the condom sheath during sexual intercourse. This method of birth control has not proven fail safe. Condoms are known to slip from the penis during sexual intercourse to allow leakage of the semen into the canal of the female leading to the unfertilized egg. Accordingly, methods have been sought to prevent such slippage and thereby protect against leakage to accomplish the end of birth control.

At present times, condoms have gained more importance because of uses other than for birth control. The proliferation of sexual diseases, particularly AIDS, has brought much concern about the dangers of the semen than with respect to preventing fertilization during sexual intercourse. Studies have shown that the trapped semen of an infected person can prevent the transmission of AIDS during sexual activity. Moreover, use of condoms to prevent AIDS has emphasized the advantages of condoms in protecting against the transmission of other sexual diseases during sexual activity. Accordingly, preventing leakage by preventing the slippage of a condom during sexual activity is an end to be desired.

Several U.S. patents disclose inventions directed to preventing such slippage or otherwise avoiding leakage.

British Patent No. 1,252,255 issued to Kennedy and published Nov. 3, 1971, discloses a condom that has a main body section of general cylindrical shape and circular cross section that is substantially smaller than the head section of the condom. The disclosure teaches of the smaller diameter body section to providing a degree of sealing against the escape of semen that is not ordinarily avoided by conventional condoms of uniform tubular cross section.

U.S. Pat. No. 4,354,494 issued to Hogin on Oct. 19, 1982, discloses a condom for preventing contraception or venereal diseases by including an elongate tubular sheath closed at one end and having a periphery about the opening of the other end to which is secured an elongate resilient retention strap. The retention strap is arranged to encircle the scrotum of the wearer and thereby hold on the sheath. The device uses a conventional bead at the periphery of the opening, and so the strap, which is made of thin rubber, is secured thereto in a fairly weak structure. Accordingly, the strap may readily tear from the condom during particularly active sexual activity. Furthermore, the retention device as taught by Hogin requires a complex manufacture of the condom and the strap which would increase the price of condoms with the possible consequence of decreasing the demand for condoms.

U.S. Pat. No. 5,111,831 issued to Foggia on May 12, 1992, discloses a rollable condom having a retention periphery at its open end. A conventional bead at the periphery of the open end is discontinuous at a notch. A hole is located opposite the notch within the wall of the condom sheath along the bead. The hole has a indentation which is centered on the hole towards the closed end of the sheath. The sheath also has a seal which is located toward the closed end of the sheath to form a circumference of a smaller diameter than the tubular sheath. When the sheath of the condom is fully unrolled onto the penis, the scrotum is positioned through the hole to provide a retention strap around the scrotum. It would appear that without the seal, this device would be easier to manufacture than the device of Hogin. But without the seal, there is even a greater opportunity for semen to leak out of the open end as the bead is not there to provide a seal at the periphery.

U.S. Pat. No. 4,955,392 issued to Sorkin introduces a different solution but with other shortcomings. Sorkin teaches use of a condom that includes a tubular length having a closed first end and an open second end. The open second end includes an integral pubic shield which is adapted to overlay the pubic area of the user. The device does not provide for a seal, although leakage may be lessened by the distance the semen has to travel in order to escape from the condom. According to the teachings of Sorkin, however, the condom is of such a complex structure as to increase its cost, and its coverage may also interfere with the pleasure of the activity when it is in use.

III. Objects of the Invention

In view of the above mentioned shortcomings of the prior art designs, it is a primary object of the present invention to provide a functional retainer ring structure that retains a condom on the penis during sexual activity.

Another object of the present invention is to provide a condom retainer ring structure that retains a condom on the penis of the wearer and seals the condom at the penis base.

Yet another object of the present invention is to provide a condom retainer ring structure that supports the scrotum to achieve increased stimulation during use.

Still yet another object of the present invention is to provide a condom retainer ring structure that may be adjusted to the circumference of the penis and/or scrotum of the wearer.

Yet still another object of the present invention is to provide a condom retainer ring structure that may be used with conventional or standard condoms, as well as a condom retainer ring structure that may be incorporated into the structure of a condom.

An additional object of the present invention is to provide a method of making a condom ring structure having the advantages described in the above objects.

SUMMARY OF THE INVENTION

A condom with a condom retainer ring structure has an elongate tubular sheath made of a resilient material that is closed at one end and open at the other. A condom retainer ring structure is attached to the sheath at the periphery of the opening. The condom retainer ring structure is comprised of two rings that are joined together by a bridge. One of the rings is Joined to the sheath at the periphery of opening. The condom retainer ring structure also includes a tab that provides a means for pulling the condom onto the penis and provides a means to identify by feel the top portion of the condom when in the rolled position.

The condom retainer ring structure may be used with a commercially produced condom, by which it is placed on the penis, and the condom retainer bridge structure 20 is placed on the penis and scrotum thereafter. In a second embodiment, a condom retainer ring structure may be manufactured independently of the rings, so that rings may be manufactured and subsequently joined to the bridge. Yet a third embodiment has rings that are one continuous funicle that is captured by and snakes through the bridge, so that the rings may be adjusted relative to one another by pulling on one ring forms a greater loop or circle with the other ring diametrically diminished thereby.

A preferred method of manufacturing a condom with the condom retainer ring structure involves a manufacturing process for making standard condoms. A continuous power-driven conveyor has a plurality of mandrels, which are caused to tip and turn in response to conveyor movement as each mandrel is sequentially carried through each step in the condom making operation.

First, the mandrel is carried to a first station, where it is dipped in a dip that is filled with liquid latex or the like in an uncured state. Second, the mandrel is carried through a drying section so that the coating from the dip is dried on the mandrel. Third, after leaving the drying station the mandrel is carried to a beading station. At the beading station, the coating adjacent to the open end of the condom is engaged by a device which rolls up a bead at the upper edge of the condom. This bead provides a beginning of the condom ring retainer structure. A cutting tool cuts the bead into two rings with a part of the bead bridging the rings. Fourth, after the cutting station, the mandrel is carried to a stripping station. At the stripping station, the condom is stripped from the mandrel by being rolled down from the mandrel.

By a second method, a bead of thinner thickness than the bead described in the former operation, may be first formed and place on the mandrel. Thereafter, dipping process may be used to form a coating. From the coating, a second bead may be formed, which is fused to the first bead at the bridge structure.

BRIEF DESCRIPTION OF THE DRAWINGS

FIG. 1 is a perspective view of a condom retainer ring structure on a condom in accordance with the present invention.

FIG. 2 is a elevational view through the open end of a condom having the condom retainer ring structure as an embodiment of the present invention.

FIG. 3 is a side view of the condom shown in FIG. 2, generally in the direction of arrow 3 of FIG. 2.

FIG. 4 is a partial side view of the present invention properly positioned on an erect penis.

FIG. 5 is an elevational view of a retainer ring structure with retainer rings spread apart from one another.

FIG. 6 is an elevational view of the retainer ring structure in accordance with the present invention.

FIG. 7 is a cross sectional view of the condom retainer ring structure shown in FIG. 6 taken roughly in the direction of arrows 7—7 of FIG. 6.

FIG. 8 is a partial side view of the condom retainer ring structure shown in FIG. 6.

FIG. 9 is a partial side view of the condom retainer ring structure shown in FIG. 8, but positioned differently on an erect penis.

DETAILED DESCRIPTION OF THE PREFERRED EMBODIMENTS

Figure 10:
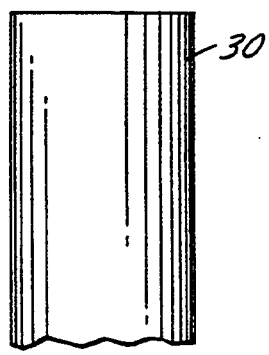
FIGS. 10-21 illustrate the method of applying the retainer ring structure to a condom sheath during manufacture, with FIG. 15 being a view taken generally in the direction of arrows 15—15 of FIG. 14.

Referring first to FIGS. 1-3, a condom with a condom retainer ring structure 10 in accordance with the present invention comprises an elongate tubular sheath 12 made of a resilient material, such as rubber. Sheath 12 is closed at one end 14, which may have a semen receptacle 16 structured thereinto. Sheath 12 has an opening 18 at an axial end of sheath 12.

A condom retainer ring structure 20, preferably also made of a resilient material, is attached to sheath 12 at the periphery of opening 18. Condom retainer ring structure 20 is comprised of two rings 22 and 24 that are Joined together by a bridge 26.

Ring 24 is joined to sheath 12 at the periphery of opening 18. It is preferred that, when the condom retainer ring structure 20 is in a relaxed state, ring 22 and 24 lie adjacent one another. Further, it is preferred that the diameter of ring 22 is generally equal to the diameter of ring 24.

Condom retainer ring structure 20 also includes a tab 28 that provides a means for pulling condom 10, including condom retainer ring structure 20, onto the penis and provides a means to identify by feel the top portion of the condom when in the rolled position. By a method later to be described, the condom 10, including the condom retainer ring structure 20, is rolled up. To use the condom 10, after it is removed from its packaging, the head of the penis is pressed against closed end 14 from the inside of the condom and the condom is unrolled along the shaft 12 until the condom ring structure is free. Because of the tab structure, the rolled up condom will be fatter as it is rolled around the tab so that the ring structure may be oriented with this in mind. Ring 24 then may be pulled down and around the scrotum to position the condom ring structure as shown in FIG. 4.

The condom retainer ring structure has been Just described as a part of a condom 10. It should be appreciated, however, that the condom retainer ring structure 20 in accordance with the foregoing description may be used with a commercially produced condom. In such a case, the condom is placed on the penis as any commercially produced condom would be placed on the penis and the condom retainer ring structure 20 is placed on the penis and scrotum thereafter. This would be done by placing both rings 22 and 24 over the head of the penis, preferably, the penis being inserted through ring 24 before ring 22 if ring 24 is larger than ring 22. Both rings are drawn to the base of the shaft of the penis close to or contiguous with the bead of the standard condom. Ring 24, if the larger of rings 22 and 24, is then manipulated to receive the scrotum therethrough, so that the ring is situated on the penis and scrotum as shown in FIG. 4. Tab 28 may be used to pull the condom retainer ring structure 20 as close to the base of the shaft of the penis as desired.

In a second embodiment of the present invention, as shown in FIG. 5., a condom retainer ring structure 120 is comprised of two rings 122 and 124. Rings 122 and 124 are joined together by a bridge 126. Bridge 126 may be manufactured independently of rings 120 and 124 so that rings 122 and 124 may be manufactured and subsequently joined to bridge 126. In this second preferred embodiment, ring 124 is shown as larger than ring 126 so that ring 124 may preferably be used to encircle the scrotum, while ring 122 may be used to encircle the penis. This condom retainer ring structure 120 may be used with a standard condom as described with respect to condom retainer ring structure 20 if not a part of the overall condom with a condom ring structure 10.

Referring now to FIGS. 6 and 7, it is seen that a condom ring retainer structure 220, as yet a third embodiment of the present invention, has the appearance of having two rings 222 and 224. Actually, as can be seen in particular in FIG. 7, rings 222 and 224 are one continuous funicle 225 that is captured by and snakes through bridge 226. Funicle 225 has two ends 225a and 225b. Funicle 225 is attached to bridge 225 at end 225a and is formed substantially in a circle 222 before entering into a passage 227 snaking through bridge 226 before re-emerging from bridge 226 and forming substantially a second circle 224 before being fixedly captured by bridge 226 at end 225b.

The structure of rings 222 and 224 and bridge 226 is such that by pulling ring 224 to form a greater loop or circle 224, ring 222 is diametrically diminished thereby. Thus the relative sizes of rings 222 and 224 may be adjusted. A stop 229 is provided to limit such relative adjustment between rings 222 and 224. Stop 229 cannot fit through passage 227 so as to limit the down sizing of ring 224. A stop may also be provided on ring 222. As can be seen in FIG. 8, the ring structure 220 of this embodiment, which may be worn with a standard condom 210, may be so situated on the penis and scrotum as to pull the scrotum in a desired attitude with the penis for greater stimulation during sexual intercourse. It should also be appreciated that the ring structure may be worn in an inverted attitude as shown by FIG. 8 relative to FIG. 9.

Preferably the rings of condom retainer ring structure 220 are also made of a resilient material. Bridge 226, may be made of a harder plastic material.

FIGS. 10–21 illustrate a preferred method of manufacturing a condom with condom retainer ring structure as shown in FIG. 1. Those of ordinary skill in the art know of a manufacturing process for making standard condoms by which a continuous power-driven conveyor has a plurality of mandrels, such as mandrel 30 of FIG. 10, depending from the conveyor in close spaced relationship. Each mandrel has dimensions to correspond to a predetermined size range for the condom. The mandrels are caused to tip and turn in response to conveyor movement as each mandrel 30 is sequentially carried through each step in the condom making operation.

Figure 11:
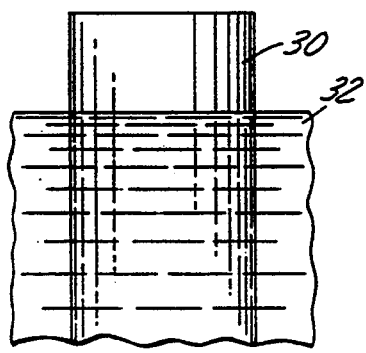
Figure 12:
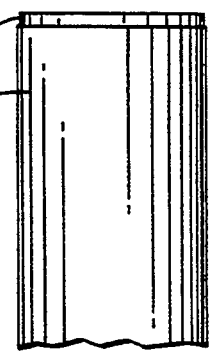
Figure 13:
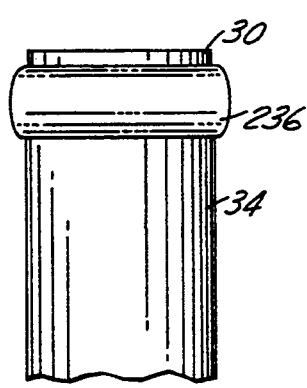
Figure 14:
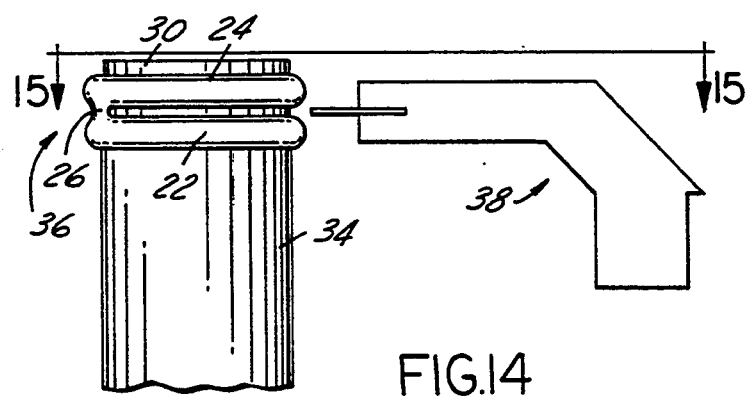

First, with reference to FIG. 10, the mandrel 30 is carried to a first station. Referring to FIG. 11, at the first station a first dip 32 is filled with liquid latex or the like in an uncured state. The conveyor causes the mandrel 30 to be dipped and coated. The conveyor raises the mandrel 30 up so that the mandrel 30 is removed from the dip and as the mandrel 30 hangs over the dip 32 to allow excess material to drip off the mandrel 30 may be returned to the dip 32.

Second, the mandrel 30 is carried through a drying section so that the coating 34 from the dip 32 is dried on the mandrel 30 while the mandrel 30 is tipped with respect to the vertical to cause the coating 34 to flow evenly as the coating 34 distributes itself over the mandrel 30. The rate of turning movement and tipping movement required to produce an even distribution varies with the coating material, but those of ordinary skill in the art would find little difficulty in establishing the proper turning and tipping necessary for ensuring coating uniformity as a consideration of the size and shape of the mandrel 30. As the mandrel 30 moves through a drying station, warm air may be blown on the coating 34 to partially dry the latex or similar fluid to substantial non-fluid condition. The conveyor may then be arranged to dip the mandrel 30 a second time in a second dip in a manner similar to the dipping at the first dip 32. A second drying station may be passed through. The drying in one or two drying stations is not intended to completely cure the coating 34 since further operations are required before curing is necessary. If two coatings are used, they should be such that they form a single homogenous condom wall.

Third, after leaving the drying station (or the second drying station each mandrel 30 is carried to a beading station. At the beading station, the coating 34 adjacent to the open end of the condom 10, which is the upper extremity of the condom 10 as it is situated on the mandrel 30, is engaged by a device, such as a rotating brush, which rolls up a bead 36 at the upper edge of the condom 10. This bead 36 provides a beginning of the condom ring retainer structure 20 of the present invention. Preferably, although the sequence of this step and the cutting operation to be described may be interchanged, after the bead is formed, the conveyor carries the mandrel 30 through a curing station. At this station, sufficient heat is applied to cure the coating on the mandrel 30. The conveyor then carries the mandrel 30 to a cutting station. A cutting tool 38 cuts the bead 36 into two rings 22 and 24 with a part of the bead 36 bridging therebetween, as can be seen with reference to FIG. 15. The width of the bridge 26 is predetermined so that the cutting tool 38 traverses a path 40 stopping short of the full circumference of the mandrel 30.

Figure 16:
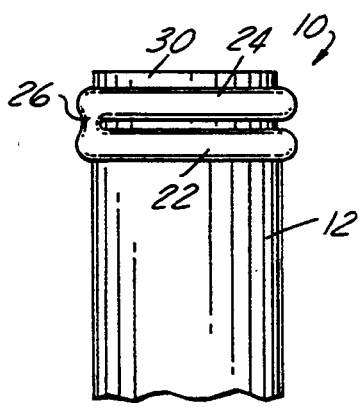
Figure 15:
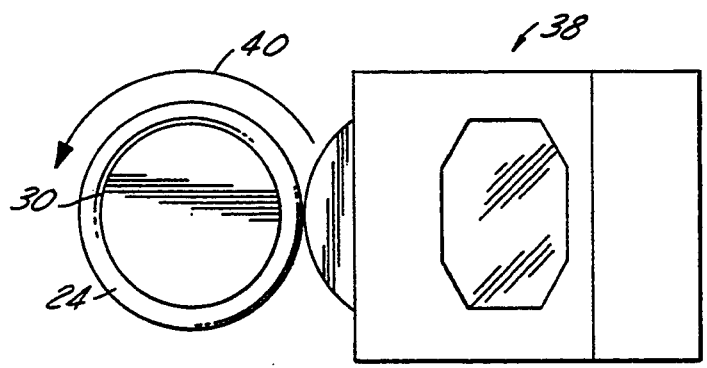
Figure 17:
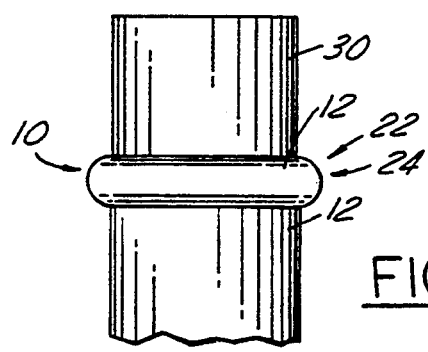
Figure 18:
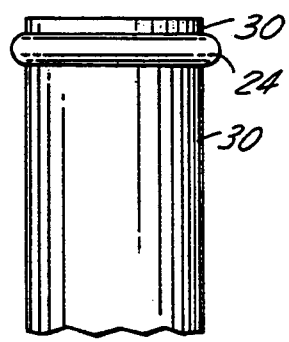
Figure 19:
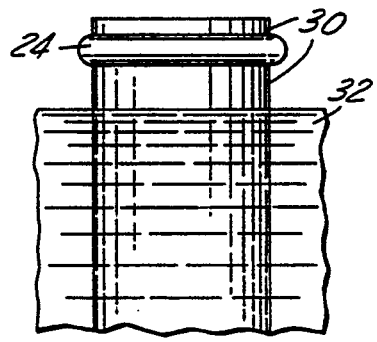
Figure 20:
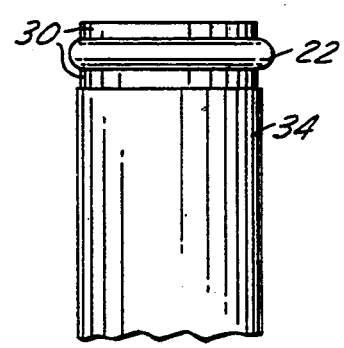

Fourth, after the cutting station, the mandrel 30, with reference to FIG. 16, is carried to a stripping station. At the stripping station, the condom 10 is stripped from the mandrel 30, referring now to FIG. 17. The stripping is accomplished by the use of brushes in a similar method that the bead is formed at the beading station. This means that, the condom shaft 12 is rolled down from the mandrel 30 until the condom 10 is rolled into the structure that is packaged. This operation may be accomplished by hand or by robotic simulation.

Figure 21:
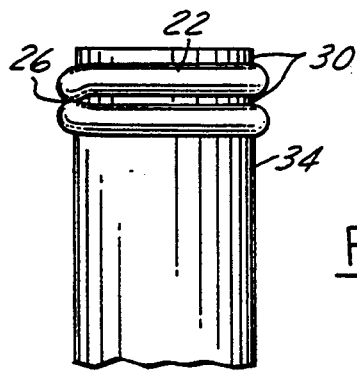

By a second method, a preformed bead 22 of thinner thickness than the bead described in the former operation, may be first placed on the mandrel 30. Thereafter, referring to FIGS. 19 and 20, the dipping process may be used to form a coating 34. From the coating 34, a second bead 24, may be formed, which is then be rolled into position to be fused, during the curing process, to bead 22 as bridge 26, all of which are shown in FIG. 21. This again will form the two ring structure 20. The condom is thereafter pulled down for packaging in the method similar to the former operation.

It should be understood that a condom in accordance with the present invention is particularly suitable for lubricants because the condom retainer ring structure 20 retains the condom better than a conventional lubricated condom, which has a tendency to slip. The resilient material specified is not in all embodiments critical, and any material having similar characteristics for use with or of the condom may be substituted therefor. It should be appreciated, for example, that the resilient characteristic of the condom may not be necessary for an adjustable condom ring structure. Any embodiment of the invention that has been described in detail may be subjected to modifications and other embodiments incorporating the inventive features. Accordingly, it is intended that the foregoing disclosure is to be considered as illustrating the principles of the present invention as an example of those features and not as a delimiting description, which is the purpose of the claims that follow.

I claim:

1. A single-piece retainer ring structure for wearing on the penis and scrotum of a male wearer, the structure comprising:
    a first ring for encircling the penis;
    a second ring adjacent said first ring, said second ring for encircling said scrotum; and
    a bridge joining said first ring with said second ring, said bridge and said first and second rings being integrally formed as a single-piece structure;
    wherein said first ring and said second ring are formed by an elongated funicle having one end attached to said bridge, said funicle being formed in a substantially circular loop and entering into and snaking through said bridge and forming said second ring of a substantially circular loop wherein said second end of said funicle is attached to said bridge.

2. The structure of claim 1, wherein the first ring may be adjusted to increase and decrease the diameter thereof, said adjustment of said first ring causing an opposite adjustment of said second ring.

3. A combination of a condom and a condom retainer ring structure, the combination comprising:
    an elongated thin-walled tubular sheath of resilient material being closed at one end and having an opening at the other end; and
    a single-piece retainer ring structure including a first ring at the periphery of said opening and surrounding said sheath;
    a second ring adjacent said first ring; and
    wherein said opening includes a continuous periphery having a continuous bead at its edge and said first ring may be slid along the extension of said sheath and off said sheath; and
    a bridge joining a portion of said first ring with a portion of said second ring;
    wherein said bridge is formed by the attachment of said first ring to said second ring; and
    wherein said first ring and said second ring are formed by an elongated funicle having one end attached to said bridge, said funicle being formed in a substantially circular loop and entering into and snaking through said bridge and forming said second ring of a substantially circular loop wherein said second end of said funicle is attached to said bridge.

* * * * *